(12) United States Patent
Bagasra et al.

(10) Patent No.: US 8,669,082 B1
(45) Date of Patent: Mar. 11, 2014

(54) SINGLE VESSEL PRODUCTION OF BUTANOL FROM BIOMASS USING ENGINEERED THERMOPHILIC MICROORGANISMS

(75) Inventors: Omar Bagasra, Orangeburg, SC (US); Kamal Chowdhury, West Columbia, SC (US); Verlie A. Tisdal, Orangeburg, SC (US); George E. Miller, III, Columbia, SC (US); Rebecca Bullard-Dillard, Orangeburg, SC (US)

(73) Assignee: Claflin University, Orangeburg, SC (US)

( * ) Notice: Subject to any disclaimer, the term of this patent is extended or adjusted under 35 U.S.C. 154(b) by 0 days.

(21) Appl. No.: 13/592,103

(22) Filed: Aug. 22, 2012

(51) Int. Cl.
*C12N 1/20* (2006.01)
*C12P 7/16* (2006.01)
*C12N 15/00* (2006.01)

(52) U.S. Cl.
USPC ......... 435/160; 435/252.7; 435/157; 435/161

(58) Field of Classification Search
None
See application file for complete search history.

(56) References Cited

PUBLICATIONS

Gottlund KL et al. Protoplast formation and cell wall regeneration in *Clostridium thermocellum*. 1988. Biotechnology Techniques. vol. 2 No. 2. pp. 137-140.*
Gokhale D et al. Isolation of intergeneric hybrids between *Bacillus subtilis* and *Zymomonas mobilis* and the production of thermostable amylase by hybrids. 1994. Biotechnology and Applied Biochemistry. 20. pp. 109-116.*
Jones DT et al. Production of Recombinants after Protopolast Fusion in *Clostridium acetobutylicum* P262. 1985. Journal of General Microbiology. 131. 1213-1216.*
Tyurin MV et al. Electrotransformation of *Clostridium thermocellum*. 2004. Applied and Environmental Microbiology. vol. 70, No. 2. pp. 883-890.*
Yu, EKC et al. Butanol production from cellulosic substrates by sequential co-culture of *Clostridium thermocellum* and *C. acetobutylicum*. 1985. Biotechnology Letters. vol. 7 No. 7. pp. 509-514.*
Pierre Schaeffer et al., Fusion of bacterial protoplasts, Journal, Jun. 1976, Proc. Natl. Acad. Sci. USA, vol. 73, No. 6, pp. 2151-2155, Microbiology.
Rollin D. Hotchkiss et al., Biparental products of bacterial protoplast fusion showing unequal parental chromosome expression, Journal, Jun. 1980, Proc. Natl. Acad. Sci. USA, vol. 77, No. 6, pp. 3553-3557, Genetics.
Errol R. Allcock et al., *Clostridium acetobutylicum* Protoplast Formation and Regeneration, Journal, Mar. 1982, Applied and Environmental Microbiology, vol. 43, No. 3, p. 719-721.
Nigel P. Minton et al., Regeneration of Protoplasts of *Clostridium pasteurianum* ATCC 6013, Journal of Bacteriology, Jul. 1983, vol. 155, No. 1, p. 432-434.
Lyang-Ja Lee-Wickner et al., Production and Regeneration of *Lactobacillus casei* Protoplasts, Journal, Nov. 1984, Applied and Environmental Microbiology, vol. 48, No. 5, p. 994-1000.
Gilles Reysset et al., Protoplast Formation and Regeneration of *Clostridium acetobutylicum* Strain N1-4080, Journal of General Microbiology, Mar. 1987, vol. 133, p. 2595-2600.

* cited by examiner

*Primary Examiner* — David J Steadman
*Assistant Examiner* — Paul Holland
(74) *Attorney, Agent, or Firm* — McNair Law Firm, P.A.; Seann P. Lahey

(57) ABSTRACT

The present invention relates to the production of biofuels by utilizing efficient biomass digestion and fermentation by a new thermophilic microorganism generated after fusion of two different bacteria *Clostridium thermocellum* and *C. acetobutylicum* and properly mutating the fused bacteria to produce biofuels and other economically important chemicals in a single vessel from lignocellulosic derived renewable biomass. All the necessary biochemical digestions and fermentation are carried out by this single thermophilic microorganism in one single vessel eliminating the need for multiple step digestion and fermentation processes, requiring multiple chambers. It also significantly reduces the rate limiting steps where increasing accumulation of alcohol, butanol and other substances become toxic to the very bacteria that produce these biofuels. The single vessel is incubated at high temperatures (45° C. or above) to eliminate the need for periodic stoppage and restarting of the process.

13 Claims, 1 Drawing Sheet

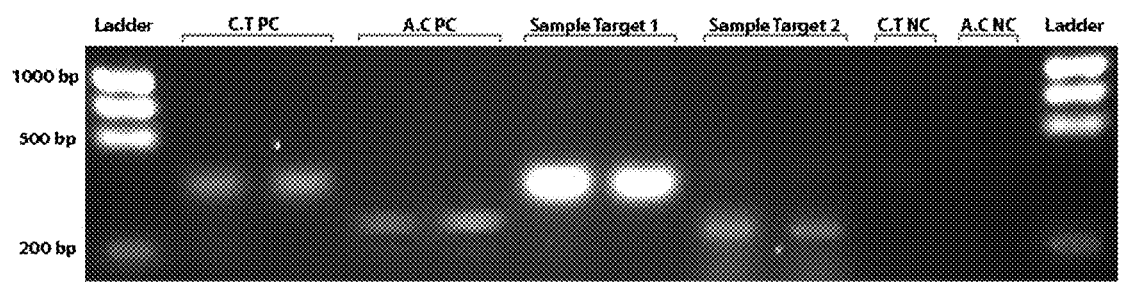

SINGLE VESSEL PRODUCTION OF BUTANOL FROM BIOMASS USING ENGINEERED THERMOPHILIC MICROORGANISMS

BACKGROUND OF THE INVENTION

1) Field of the Invention

The present invention relates to the production of biofuels, such as butanol, from renewable biomass through a fermentation process using genetically engineered thermophilic microorganisms. Instead of transferring enzyme coding genes in cassettes by recombinant-DNA technology, the present invention involves an entirely new created microorganism resulting from the fusion of two species of Clostridia, to produce a new strains designated C. thermolignocelluloticum. This new life form can carry out fermentation of biomass in a single vessel at relatively thermophilic temperatures (i.e. 45° C. to 65° C.). Use of this microorganism eliminates the need for multistep, multi-vessel, low temperature reaction system and brings about a single vessel system for the direct conversion of lignocellulosic biomass to butanol and other economical important chemicals.

2) Description of Related Art

World oil production capacity reached a peak in 2006 but the demand for oil is continuing to rise. Therefore, it is essential to look for alternative renewable sources of fuel to meet exiting energy demands. In 2007, there were 1.8 million alternative fuel vehicles sold just in the United States, indicating an increasing popularity of alternative fuels. In addition to searching for viable alternate fuels, efforts have been ongoing to reduce the consumption of fossil fuel vehicles. In 2007, there were more than 6.65 million flexible-fuel vehicles (FFVs) on U.S. roads. By the end of 2010, that number increased to nearly 8.1 million. Three U.S. automakers (GM, Chrysler and Ford) have committed to increasing production of FFVs annually. GM, for example, has said that half of all its vehicles could be FFVs by 2012, pending availability of E85 bio fuel. FFVs are capable of operating on E85, which is a blend of 85 percent ethanol and 15 percent gasoline. Ethanol is a common ingredient in most gasoline formulations as well, but is only used in quantities of 5 to 10 percent to reduce smog-forming emissions and greenhouse gases.

The increase in E85-capable vehicles has gone hand-in-hand with an increase in the availability of E85 fuel. In March 2008, there were about 2,800 E85 fuel stations in the United States, with an ever-increasing number of additional stations scheduled to come online in the coming years. In contrast, in 2000 there were only 14 E85 stations in the US. However, this is still a small number compared to over 200,000 gas stations in the United States. Accordingly, what is needed is to look for an alternative fuel that uses the same existing 200,000 gas stations and can be used by the current gasoline vehicles without significant alteration. Currently, there are two fuels that fit this definition. One is compressed natural gas (CNG) and another one is Bio-Butanol. The CNG cars are very common in many Asian cities and some parts of Europe where natural gas is abundant. Several automakers will be introducing a duel fuel car that uses oil and CNG simultaneously. Although there are numerous manufacturers that offer factory-built natural gas trucks, step-vans, transit buses and school buses, there are fewer options for consumers who need light-duty cars, vans and pickup trucks. Currently, the only natural gas light-duty vehicle manufactured in the U.S. is the Honda Civic GX. Of note, public transportation across the country has been using CNG for decades. And currently, about 12-15% of public transit buses in the U.S. run on natural gas (either CNG or LNG—liquefied natural gas). That number is growing, with nearly one in five buses on order today slated to run on natural gas. States with the highest consumption of natural gas for transportation are California, New York, Texas, Georgia, Massachusetts and Washington D.C.

With the world's oil supply declining and increasing environmental concerns, there has been a push to develop alternative-fuel vehicles. In addition, to FFV vehicles, hybrid vehicles have become increasingly popular, with more than 200,000 units sold annually in the U.S. in 2005 and 2006 and 350,000 in 2007. Sales will most likely continue to increase as the range of hybrid choices grows: Some 44 hybrids are expected to be on sale by 2012, up from 15 in 2008, according to *J. D. Power and Associates Automotive Forecasting*. Hybrid vehicle sales are expected to grow from approximately 212,000 vehicles in 2005 to about one million by 2012.

Presently, petroleum is the major source of energy due to its high energy density, easy transportability and relative abundance. About 16% of petroleum, which is not used for energy, is also the essential base material for many chemical products, including plastics, pharmaceuticals, solvents, fertilizers, pesticides, and tar for road constructions. Known oil reserves are typically estimated at around 190 km$^3$ (4.76 trillion barrels). Consumption is currently around 84 million barrels ($13.4 \times 10^6$ m$^3$) per day, or 4.9 km$^3$ per year. Therefore, if current demands remain the same, the remaining oil supply will last for about 120 years. Due to increasing demands from developing nations like China, India and Brazil and no increased production, the oil prices are predicted to significantly go up in the coming decades.

Chemically, petroleum is a mixture of a very large number of different hydrocarbons; the most commonly found molecules are linear or branched alkanes, cycloalkanes, aromatic hydrocarbons, or more complicated chemicals like asphaltenes. Each petroleum variety has a unique mix of molecules, which define its physical and chemical properties, like color and viscosity.

The alkanes are saturated hydrocarbons with straight or branched chains which contain only carbon and hydrogen and have the general formula $C_nH_{2n+2}$. They generally have from 5 to 40 carbon atoms per molecule, although trace amounts of shorter or longer molecules may be present in the mixture.

The alkanes from pentane ($C_5H_{12}$) to octane ($C_8H_{18}$) are refined into petrol, the ones from nonane ($C_9H_{20}$) to hexadecane ($C_{16}H_{34}$) into diesel fuel, kerosene and jet fuel. Alkanes with more than 16 carbon atoms can be refined into fuel oil and lubricating oil. At the heavier end of the range, paraffin wax is an alkane with approximately 25 carbon atoms, while asphalt has 35 and up, although these are usually broken down by modern refineries into more valuable products. The shortest molecules, those with four or fewer carbon atoms, are in a gaseous state at room temperature. They are the petroleum gases.

These different molecules are separated by fractional distillation at an oil refinery to produce petrol, jet fuel, kerosene, and other hydrocarbons. For example, 2,2,4-Trimethylpentane (isooctane), widely used in petrol, has a chemical formula of $C_8H_{18}$ and it reacts with oxygen exothermically. $(2C_8H_{18}(l) + 25O_2(g) \rightarrow 16CO_2(g) + 18H_2O(g) + 10.86$ MJ/mol (of octane)).

The amount of solar energy received at the earth's surface is $2.5 \times 10^{21}$ Btu/year, which far exceeds the present human usage of $2.0 \times 10^{17}$ Btu/year. The amount of energy from the sun which is stored as carbon via photosynthesis is 10 times the world usage. A significant amount of that form of solar energy captured by photosynthesis and stored in biomass can contribute substantially in conversion of transportation fuel at costs competitive with fossil fuel.

Approximately 70% of plant biomass is locked up in 5- and 6-carbon sugars. These sugars are found in lignocellulosic biomass, which is comprised of mainly cellulose, which is a homologous polymer comprised of long chains of glucose; less so, hemicelluloses which is a heterologous polymer of 5- and 6-carbon sugars; and least of all lignin, which is a complex aromatic polymer. A potentially vast source of renewable energy lies within these lignocellulosic biomass. Each year, more than 40 million tons of inedible plant material, including leaves, stems, and stalks from sources such as corn fiber, corn stover, sugarcane bagasse, rice hulls, woody crops, and forest residues. Also, there are multiple sources of lignocellulosic waste from industrial and agricultural processes, e.g., citrus peel waste, sawdust, paper pulp, industrial waste, municipal solid waste, and paper mill sludge. In addition, dedicated energy crops for biofuels could include perennial grasses such as switchgrass and other forage feedstock such as miscanthus, bermuda grass, elephant grass, etc—much of which is unexploited, and inexpensive and mainly thrown away. Turning this waste lignocellulosic biomass into biofuels, such that it will not interfere with food supplies like the manufacturing of ethanol from corn, is a logical solution.

The woody material that gives plants their rigidity and structure comprises three main types of carbon-based polymer—cellulose, hemicellulose and lignin—collectively called lignocellulosic biomass. When digested via fermentation, these polymers yield chemical components that can be used to make biofuels. Cellulose is a difficult substrate for enzymatic degradation because of its physical properties. Cellulose molecules are composed of chains of $\beta$-1,4-linked glucose units. The chains are insoluble and form fibrils in which cellulose chains are arranged in parallel bundles that are very stable due to inter-chain hydrogen bonds and Van der Waals interactions between the pyranose rings. Cellulose is largely insoluble and exists in crystalline microfibrils that make the sugars hard to digest. These cellulose microfibrils are a variety of sugars, making it more complicated to convert to a single product such as ethanol or butanol. The covalent chemical bonds that hold lignin's polymers together make it very difficult to break down. Added to that, the composition of lignin varies from plant to plant, and the true structure of this sturdy material remains unknown.

The microbial degradation of cellulose is carried out by the concerted action of different glycoside hydrolases. According to their mode of action, celluloses are subdivided into endo- and exoglucanases. Endoglucanases randomly cleave the cellulose chains at exposed positions and create new ends, while exoglucanases degrade the polymeric chain from either the reducing or the non-reducing end, producing cellobiose as the main product.

Previously, the best way to break apart these lignocellulosic materials and extract their chemicals for fuel production involves heat and strong chemicals. This is a complex process wherein: once source material has been mechanically ground up, the biomass requires pretreatment using heat, acid or ammonia to rip apart the lignin and expose the cellulose and hemi-cellulose inside. Enzymes can then penetrate the biomass and liberate the sugars, which are then fermented and distilled to produce alcohols.

Methane gas, methanol, ethanol, propanol and butanol are the main types of biofuels that can be considered either to blend with or replace gasoline. Mainly due to already existing technology, ethanol is presently considered the most popular biofuel and is blended with gasoline at concentrations ranging from 1 to 85%. Such mixtures are often referred to as gasohol. However, ethanol use in the US is currently limited due to its unavailability from inadequate production to limited distribution. It is currently available in only a small percentage of US fuel pumps.

Although ethanol is the predominant biofuel at this time, (used as E85 as mentioned above) its use has a number of drawbacks when compared to butanol. The potential quantity of butanol that could be produced from cellulose is over an order of magnitude larger than that producible from corn. In contrast to the corn-to-ethanol conversion, the cellulose-to-butanol route involves little or no contribution to the greenhouse effect and has a clearly positive net energy balance (~ten times better). Butanol is a four-carbon alcohol and thereby yields 25% more energy than ethanol as measured in Joules/gallon (or liter). This means that its energy output is closer to gasoline and can be used as a replacement for gasoline. Bio-butanol, like ethanol, is produced either from conventional crops, such as corn, or from lignocellulosic feedstock. Some advantages that butanol has over ethanol as a transportation fuel are a higher energy density, which provides more miles traveled per gallon of fuel, and a lower tendency to absorb water, which provides more flexibility for transporting butanol and blending it with gasoline. Unlike ethanol, butanol does not need to be mixed with gasoline for use in internal combustion engines and therefore it can be an adequate substitute for gasoline. Furthermore, butanol production also yields useful byproducts such as hydrogen gas that can be used in fuel cell technology and carbon dioxide and hydrogen than can be marketed as gas for other industrial application such as the production of dry ice and chemicals. Furthermore, butyric acid can be used as a base for producing jet fuel.

Unlike ethanol, butanol can use the existing delivery infrastructure such as tanker trucks, pipelines and service stations. Butanol is less explosive, less evaporative (bp 117° C. as compared to ethanol by of 78° C.) and less corrosive than ethanol and, therefore, safer to handle and distribute. Local/Regional production means less dependence on long-distance fuel supply therefore the systems would be less prone to bioterrorism and more favorable for homeland security.

Butanol was tested in a 1992 Buick without modifying the car engine as 100% gasoline replacement in a 10,000-mile trip across the United States. The fuel mileage of 20-26 miles per gallon of butanol was much better than that for gasoline for the same vehicle that gave 22 miles/gallon. That was over 9% increase. E-Test facilities in 10 states revealed that use of butanol yielded an average reduction of hydrocarbons of 95%, the reduction of carbon monoxide was 97%, oxides of nitrogen were reduced by 37% and the background of carbon dioxide was only 14.7% and carbon monoxide emission was to 0.01%.

To meet current gasoline needs with butanol, it will be necessary to utilize all available biomass including wheat stems, corn stover (the stalks and leaves) and wood shavings from logging, bagasse (sugar cane residues), and other agricultural and forestry biomass described above to produce biofuel. A current disadvantage of butanol versus ethanol is that it is more expensive to produce using existing technology, making it less competitive with ethanol.

Accordingly, it is an object of the present invention to develop a more efficient and cost-effective butanol production process to reduce dependence on fossil fuels.

SUMMARY OF THE INVENTION

The above objective is accomplished according to the present invention by providing a thermophilic bacterial chimera comprising a fusion of two species of Clostridia, said fusion capable of breaking down complex carbohydrates into glucose and converting glucose into biofuel.

According to the invention, the fusion further has the ability to break down a cellulosic biomass into glucose, convert glucose into butyric acid, $CO_2$ and $H_2$ and, convert butyric acid into butanol at thermophilic temperatures ranging from 45° C. to 65° C.

According to the invention, the two species of Clostridia comprise Clostridium acetobutylicum (ATCC 824) and Clostridium thermocellum (ATCC 27405).

According to the invention, the fusion comprises Clostridium thermobutanolicum deposited with the ATCC on Dec. 22, 2011 and designated as MF 14ACpTC.

According to the invention, the biofuel is selected from the group consisting of methanol, ethanol, propanol, butanol, and methane gas.

According to the invention, the biomass is selected from the group consisting of cellulosic biomass, lignocellulosic feedstock, plant matter.

According to the invention, the biomass comprises wheat straw and/or pulping liquor.

The above objective is further accomplished according to the present invention by providing a single-step, single-vessel method of converting a biomass into a biofuel, said method comprising the steps of (a) combining a biomass comprised of complex carbohydrates and a thermophilic anaerobic biocatalyst microorganism in a single reaction chamber; (b) permitting the biocatalyst microorganism to digest complex carbohydrates found in the biomass into glucose and other monosaccharides; and (c) fermenting the glucose and other monosaccharides produced in step (b) into a biofuel.

According to the invention, the complex carbohydrates include cellulose.

According to the invention, the biomass contains cellulose.

According to the invention, the biomass comprises a lignocellulosic feedstock.

According to the invention, the biomass is derived from plant matter.

According to the invention, the plant matter is wheat straw and/or pulping liquor.

According to the invention, the biofuel is selected from the group consisting of methanol, ethanol, propanol, butanol, and methane gas.

According to the invention, the biofuel is butanol.

According to the invention, the fermentation of step (b) takes place at a temperature at which the butanol evaporates and under controlled vacuum conditions, such that the butanol may be continually evaporated and collected via a differential distillation and condensation process.

According to the invention, the continual evaporation and collection processes prevents the level of butanol from reaching levels toxic to the biocatalyst microorganism.

According to the invention, the digesting and fermenting of steps (b) and (c) take place at thermophilic temperatures ranging from 45° C. to 65° C.

According to the invention, the thermophilic anaerobic biocatalyst microorganism comprises a fusion of two species of Clostridia.

According to the invention, the two species of Clostridia comprise Clostridium acetobutylicum (ATCC 824) and Clostridium thermocellum (ATCC 27405).

According to the invention, the fusion comprises Clostridium thermobutanolicum deposited with the ATCC on Dec. 22, 2011 and designated as MF 14ACpTC.

The above objective is further accomplished according to the present invention by providing a method of producing a Clostridial chimera comprising the steps of (a) co-culturing colonies of Clostridium acetobutylicum (ATCC 824) and Clostridium thermocellum (ATCC 27405); (b) preparing the co-cultured colonies of step (a) into protoplast; (c) fusing the protoplasts and incubating resulting protoplastic culture; and, (d) selecting those colonies having morphologically distinct characteristics as compared to Clostridium acetobutylicum (ATCC 824) and Clostridium thermocellum (ATCC 27405).

According to the invention, the co-culturing of step (a) comprises a first incubation at 45° C. and a second incubation in hypertonic media at 30° C.

According to the invention, the preparation of step (b) comprises the steps of centrifuging the co-culture and resuspending the bacteria in a protoplasting medium.

According to the invention, the protoplast fusion of step (c) comprises suspension in a polyethylene glycol (PEG) solution.

According to the invention, the colonies selected in step (d) are capable of breaking complex carbohydrates into glucose and converting glucose and other simple sugars into biofuel.

According to the invention, the colonies selected in step (d) are capable of breaking down a cellulosic biomass into glucose, converting glucose into butyric acid, $CO_2$ and $H_2$ and, converting butyric acid into butanol at thermophilic temperatures ranging from 45° C. to 65° C.

According to the invention, the method further comprises step (e) wherein the colonies selected in step (d) are modified by mutagenesis to be more thermophilic.

According to the invention, the mutagenesis step comprises the introduction of random mutations with the —NOPD (4-Nitro-ortho-phenylenediamine).

According to the invention, the fusing of protoplasts and incubating resulting protoplastic culture in step (c) is performed at temperatures ranging from 45° C. to 65° C.

BRIEF DESCRIPTION OF THE DRAWINGS

The construction designed to carry out the invention will hereinafter be described, together with other features thereof. The invention will be more readily understood from a reading of the following specification and by reference to the accompanying FIGURE, wherein:

FIG. 1 shows the identification of Clostridium thermocellum (CT PCT), Clostridium acetobytercum and the chimera strain Clostridium thermolignocellulaticum created by fusion showing the presence of both strains by PCR.

It is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described in the specification and by the appended claims. CL DETAILED DESCRIPTION OF A PREFERRED EMBODIMENT Clostridia is a diverse group of gram-positive, rod-shaped anaerobes that include several toxin-producing pathogens (notably, Clostridium difficile, Clostridium botulinum, Clostridium tetani, and Clostridium perfringens) and a large number of terrestrial species that produce acetone, butanol, ethanol, isopropanol, and organic acids through fermentation of a variety of carbon sources. Isolates of Clostridium acetobutylicum was first identified between 1912 and 1914, where Chaim Weizmann used this bacteria to develop industrial starch-based acetone, butanol, and ethanol (ABE) through fermentation, essentially to produce acetone for gunpowder production during World War I. During the 1920s and 1930s, the industrial level fermentation was utilized to produce butanol. However, more cost-effective production by petrochemical processes in the 1950s led to the decline of the ABE process, except in very few nations (i.e. Brazil and the USA). In the 1970s, the crude oil prices rose due to oil embargo by Saudi Arabia and other OPEC nations that stimulated the renewed interest in the fermentation based ABE process and in the genetic manipulation of C. acetobutylicum and other related species to improve the yield and purity of solvents from wide varieties of starch substrates.

Based on temperature tolerance, these microbes can be classified as: psychrophiles, that can tolerate temperature ranges −2 to 20° C. with optimum range of 12-14° C., psychrotroph—those that can tolerate temperature ranges 0 to 32° C. with optimum range of 21-24° C., mesophiles—those that can tolerate temperature ranges 10 to 38° C. with optimum range of 30-38° C., thermophiles—those that can tolerate temperature ranges 39 to 72° C. with optimum range of 45-65° C., and hyperthermophiles or extremothermophiles—those that can tolerate temperature ranges 65 toll 0° C. with optimum range of 80-100° C.

*Clostridium acetobutylicum* (ATCC824 strain), was isolated in 1924 from garden soil in Connecticut. This strain is closely related to the historical Weizmann strain and is one of the best-studied solventogenic clostridia. The ATCC824 strain has been characterized from a physiological point of view and used in a variety of molecular biology and metabolic engineering studies in the United States and in Europe. This strain is known to utilize a wide range of monosaccharides, disaccharides, starches, and carbohydrate substrates, such as inulin, pectin, whey, and xylan. However, like the rest of the well-studied solvent-producing clostridial strains, it does not degrade cellulose, the main sugar component in lignocellulosics, which from an economic point of view are among the most interesting substrates for solvent production. Physical mapping of the genome demonstrated that this strain has a 4-Mb chromosome with 11 ribosomal operons and harbors a large plasmid, about 200 kb in size, which carries the genes involved in solvent formation. Much work has been done to elucidate the metabolic pathways by which solvents are produced and to isolate solvent-tolerant or solvent-overproducing strains. Genetic systems have been developed that allow genes to be manipulated in *C. acetobutylicum* ATCC 824, and these have been used to develop modified strains with altered solventogenic properties.

Sequence analysis of the genome of *C. acetobutylicum* ATCC 824 has indicated the presence of a gene cluster containing 10 unidirectionally transcribed genes that are predicted to encode secreted proteins with cohesin or dockerin modules. These modules are typically found in cellulosome—a large extracellular complex that is specialized in the degradation of cellulose. Cellulosome is produced by a number of anaerobic microorganisms, including Clostridial species. Dockerin modules, usually located at the C termini of the enzymatic cellulosomal subunits, consist of two duplicated sequences of, on average, 22 amino acids each.

As described above, butanol production through fermentation was first achieved during the First World War. The acetone, butanol and ethanol (ABE) fermentation method used *C. acetobutylicum*. In the past, only one organism was used in ABE fermentation method for butanol production and simple sugars were provided as the base material. For this purpose sugars were produced either by vigorous chemical treatments of lignocellulosic biomass or rarely by fermentation using other microorganisms. The yield from this process was 1.3 gallons/bushel of corn and thus it was not economically attractive. In 1993, Jain et al of Michigan Biotechnology Institute (MBI) developed an asporogenic mutant strain of *C. acetobutylicum* by mutagenizing with ethane methane sulfonate (U.S. Pat. No. 5,192,673). Although butanol production levels slightly improved, production of other solvents, such as alcohols, impeded the efficient butanol production due to the toxic effects of the by-products on the enzymatic activities of the microorganism. Improved fermentation processes were later developed to address this problem where two organisms *C. tyrobutyricum* and *C. acetobutylicum* were used. This increased the yield to 2.5 gallons/bushel, finally making butanol a more attractive biofuel. *C. tyrobutyricum* was genetically engineered to shut down the acetone production pathway, resulting in butyric acid production alone that could then be converted to butanol. Additionally, use of fibrous bed bioreactor (U.S. Pat. Nos. 5,563,069 and 5,753, 474) technology for both organisms allowed immobilized continuous cell growth and production of sole solvent production as butanol. Lignocellulosic breakdown was carried out either chemically or enzymatically as a separate step in the process.

Cellulolytic Clostridia—*Clostridium thermocellum* (ATCC 2740 strain) is an anaerobic thermophile (optimal growth at 55° C. and produces and secrete large cellulolytic complexes (called cellulosomes) that efficiently degrade cellulose and related plant cell wall polysaccharides. The cellulolytic complexes secreted by this microbe contain various enzymes, which are tightly bound to a large protein devoid of enzymatic activity called scaffolding and have very high activity on crystalline cellulose. These complexes contain various enzymes, which are tightly bound to a large protein devoid of enzymatic activity called scaffolding. The catalytic subunits participating with cellulosomes are comprised mainly of cellulases. As do most species of cellulolytic bacteria, *C. thermocellum* grows rather slowly, even on cellobiose, the major product released by cellulosomes on cellulose. Its catabolic pathways are adapted to low carbon flow, which is characteristic of growth on cellulose, and the main products of the metabolism are acetate, lactate, and ethanol.

On the contrary, *Clostridium acetobutylicum* is unable to grow on crystalline cellulose, although its genome contains a large cluster of genes encoding cellulolytic enzymes and a scaffoldin. Interestingly, it has been shown that the bacterium produces small amounts of a 665-kDa cellulosome devoid of activity towards crystalline cellulose and is poorly active on carboxymethyl cellulose or phosphoric acid-swollen cellulose. On the other hand, *C. acetobutylicum* grows much faster than *C. thermocellum*.

Therefore, these two anaerobic Clostridia—*C. cellulolyticum* and *C. thermocellum*—display interesting complementary properties. The combination of both cellulolytic and solventogenic phenotypes in a single bacteria is an attractive challenge. The strategy chosen by many investigators is cloning and expressing the genes encoding various functional cellulosome genes or mini cellulosome in *C. acetobutylicum* isolated from *C. cellulolyticum* or *C. thermocellum*. There have been numerous attempts with limited success by utilizing recombinant-DNA technologies to develop a combined, selected, enzymatic transfer from *C. cellulolyticum* or *C. thermocellum* to *C. acetobutylicum*. One of the major reasons of the limited success in the use of recombinant technology to develop a suitable *C. acetobutylicum* is the disruption in the balanced expressions of various genes or gene cassettes. The life cycle of these bacteria, like any other life forms is a complex choreography and very difficult to mimic precisely by recombinant technology, gene transfer or transfection based methods. Therefore, the plasmid based expressions of numerous enzymes in the cellulosome complex are generally not compatible with the highly ordered expressions of series of metabolic events and pathways that are finely elegantly regulated by precise feedback inhibition/activation metabolic operations of C. acetobutylicum, resulting in cellular failure.

The present invention utilizes a novel approach to create a chimera species of Clostridium by fusing the two organisms and allowing the natural selection process of the gene complementation and exchange to occur. It is similar to the fertilization process that commonly takes place via sexual reproduction in eukaryotes and, although rare, amongst the prokaryotes. Therefore, in order to facilitate the hybrid formation, protoplasts were first prepared of each of the microorganisms and then fused the two species of Clostridia by PEG fusion technology. This process allows the two to interact at the genomic and epigenetic levels, creating genetic chimera. Successful hybrids were selected through a screening process and subsequently analyzed for butanol and other products by end point analyses by HPLC. Since, C. acetobutylicum is a mesophile and C. thermocellum is a thermophile, it was important to introduce mutations in the chimera genetic structures so the hybrid microbe can optimally grow at a specific thermophilic temperature. After numerous adaptation processes, genetic chimera were generated that were thermophilic and grew well at 45° C. Referring to FIG. 1, the chimera formation was validated by specially designed PCR and subsequently by sequencing.

The process of butanol production from lignocellulosic feedstock by fermentation has previously been a complicated multi-step process requiring more than one bacterium in several separate reactor tanks. This processes is time consuming and inefficient to successfully meet the national fuel production needs in replacing gasoline. In the past, this process requires multiple steps and two-step fermentation with various phases of preparations: milling, hydrolyses, chemical treatments at high temperatures, reutilizations of the chemicals, etc. and fermentation of the biomass to provide the butanol. Grains contain starch that cannot be used directly by microorganisms, and thus need to be broken down to fermentable sugar by a three-step process. First, grains are reduced in size by grinding or milling into small grains. Water is added to the grains and then pre-boiled up to 60° C. to gelatinize the grains. At this stage alpha amylase is added to allow break down of starch molecule to release simpler carbohydrates to form mash. The mash is then boiled for 30 minutes to bring all the remaining starch into soluble form. In the post-boiling stage, fresh alpha amylase is reintroduced (since the boiling has denatured the previous enzymes) to breakdown the remaining starch molecules into dextrins (simple carbohydrates). The mash is then cooled to 35° C.; microorganisms and beta amylase are added. Beta amylase converts dextrin to glucose for microorganism's consumption to ferment to butanol. Butanol is then separated through a series of complex distillation process. During the fermentation process, alcohol concentrations reaches levels that become stressful for microorganisms cells and eventually leads to growth inhibition and cell death occurs. In addition, the fermentation process itself is exothermic and releases heat, further hindering the optimal temperature for the bacterial growth. This stress affects the efficiency of butanol production from biomass and severely limits production capacity.

The three major limiting steps in the prior art technology for the production of butanol from biomass are: 1) use of multistep processes that are cumbersome and inefficient, 2) alcohols developed during the fermentation process become toxic to the microorganism at 10-15% levels making the process rate limiting, and, 3) separation of alcohols and other products are carried out at relatively lower temperatures making the conversion process very difficult and inefficient.

Development of the new "single-step" bacteria strain of the present invention is able to make the process simple and efficient by reducing the efforts and number of steps involved. The present invention refines the process by: a) The fusion of two bacteria 1) C. thermocellum (a thermophile) with the ability to break down complex carbohydrates into glucose and 2) C. acetobutylicum (a mesophile) which has the capability to convert glucose and other simple sugars into butanol, butyric acid, $CO_2$ and $H_2$; and, b) Utilizing randomized mutations to develop strains that can function at relatively higher (thermophilic) temperature. Accordingly, a new strain of bacteria has been developed, tentatively named as Clostridium thermobutanolicum, that has the ability to break down complex carbohydrates into glucose, conversion of glucose to butyric acid, $CO_2$ and $H_2$ and, conversion of butyric acid to butanol at thermophilic temperatures (45° C. to 65° C.). Due to the effectiveness at producing butanol in a single reactor vessel, the present invention provides an economical and practical way for large-scale production of biofuel.

The present invention thus overcomes all three major limitations with the prior art method by combining the genetic materials of two important strains of Clostridium—C. thermocellum (a thermophile) and C. acetobutylicum (a mesophiles) into a new strain and converting the new fused strain into a thermophilic strain—Clostridium thermobutanolicum—by mutagenesis that can be utilized for converting biomass to butanol into a single process and in a single reaction chamber.

Since, the present invention utilizes fermentations at higher temperatures and controlled vacuum conditions where butanol is fermented by a thermophilic microorganism at a temperature that will allow evaporation of toxic alcohols such as butanol, allowing for the continual evaporation and collection of alcohols via the differential condensation process is provided so that the level of alcohol never reaches toxic levels to limit the fermentation process.

Accordingly, the present invention is directed to a single vessel reactor containing a new thermophilic Clostridium microorganism—Clostridium thermobutanolicum—that possesses the capabilities to digest complex carbohydrates found in biomass into glucose and other monosaccharides, which subsequently are fermented into butanol, as well as and other soluble byproducts and gases such as carbon dioxide and hydrogen. Due to the thermophilic nature of the microorganism (high temperature processing), butanol and other by products can continuously be evaporated and collected by a simple differential distillation and condensation cooling processes. Other gases can be separated via a simple gaseous density gradient system. In this construction and arrangement, an efficient production of butanol from biomass can be sustained.

Growth Medium for the Thermophiles

The preferred growth medium is CM4 media, which is used for many thermophiles and contains the following ingredients for one Liter of the growth medium, as set forth in table 1 below:

TABLE 1

| | |
|---|---|
| $KH_2PO4$ | 1.5 g |
| K2HPO4 | 2.9 g |

TABLE 1-continued

| | |
|---|---|
| Sodium thioglycolate | 0.5 g |
| MgCl$_2$, 6H$_2$O | 0.180.75 g |
| Yeast Extract | 5.0 g |
| Lignocellulosic source (Cellubiose: Calbiochem)) | 6.0 g |
| CaCl2 | 13.2 mg |
| NaCl | 1.0 g |
| Resazurin (1%) | 0.2 ml |
| FeSO$^4$(1.25% solution) | 0.1 ml |
| (NH4)$_2$ SO$_4$ | 1.3 g |
| Distilled deionized water | 1.0 L |

For solid culture we add 20 g of Agar/L. A note of caution: This medium contains sodium sulfide, and hydrogen sulfide production will occur, especially upon prolonged boiling. Hydrogen sulfide is hazardous and preparation of this medium should be done in a chemical hood.

Mix all the ingredients and boil until reduced indicated by a change from red to colorless. Allow to partially cool around 28° C. and tube under 97% Nitrogen, 3% hydrogen and cap with butyl rubber stoppers. Autoclave at 121° C. for 15 minutes.

Fusion of *Clostridium* Species and Chimera Production

Colonies of *Clostridium acetobutylicum* (ATCC 824) and *Clostridium thermocellum* (ATCC 27405) were picked from their respective solid media and inoculated in their respective liquid media. These colonies were incubated for 24 to 72 hour at 45° C. Then, both cultures were inoculated into amino acid supplemented hypertonic media (see below for the formula) and cultured overnight at 30° C. One milliliter from the *C. acetobutylicum* and *C. thermocellum* cultures were mixed in a 15 mL tube and incubated for another 24 hour. Then, about 1 mL of the mixed culture was added to 10 mL of fresh hypertonic medium and incubated for 6 to 8 hours at 30° C. The culture was then centrifuged at 4° for 20 minutes at 16000 rpm. The bacteria was re-suspended in 10 mL of protoplasting medium containing 100 µg/mL of lysozyme (see below for detail formula) and left undisturbed for 30 minutes at 30° so that virtually all bacteria were transformed to protoplast. The suspension was then centrifuged at 4° C. for 20 minutes at 16000 rpm, and the protoplast was resuspended in the same volume of protoplasting medium. The protoplast was centrifuged again at 4° for 20 minutes at 16000 rpm, and the protoplast was resuspended in 1 mL of protoplasting medium. This protoplasting culture was then diluted with 10 mL of 40% solution of Polyethylene glycol (PEG with molecular weight of 6000) in distilled water, and visible aggregation of the protoplasts was observed immediately. About 3 µL of the above solution was inoculated on a solid CM4 medium and incubated for 24 to 72 hours at 45° C. to 60° C. The colonies were picked and inoculated in CM4 culture media and incubated for 24 to 72 hours at 45° C. to 60° C. The colonies were picked on the bases of morphological distinct characteristic (different from *C. acetobutylicum* and *C. thermocellum*). The fused bacteria were cultured in liquid media at 45° C. and butanol productions were measured by High Performance Liquid Chromatography (HPLC, Elite LaChrome). The fused bacteria were further modified by mutagenesis in order to adopt them further into thermophilic (higher temperature) condition. Mutant (4-NOPD+Butanol) was added to some of the CM4 culture solution and incubated at the same conditions.

Mutations of the Chimera Species: Random mutations were introduced in the chimera of *C. thermocellum* and *C. acetobutylicum* with 4-NOPD (4-Nitro-ortho-phenylenediamine). Different concentrations of 4-NOPD-varying from 0.1 mg/ml and 0.02 mg/ml of 4-NOPD were used. The mutagenesis was performed using the preincubation (20 min) procedure at 37° C., with the addition of 100 µl of each of the chimera bacteria strain grown overnight (~1-2×10$^9$ cells/ml). Next day the bacteria cultured were plated and incubated again at 45° C. in anaerobic incubator and the development of colonies were observed for 5-10 days. The colonies were screened visually and each colony was inoculated in CM4 media and cultured for three days in anaerobic chamber at 45° C. High Performance Liquid Chromatography (HPLC) analyses were carried out for production and concentration of various chemicals produced in the supernatants of the cultures. The bacterial cultures that exhibited the highest levels of butanol or byteric acid were selected for further study.

The results were analyzed using HPLC again to examine for higher butanol yield. Several concentrations of butanol were obtained as follows: SEm1; 38.9 mmol/l of butanol, SE2; 28.66 mmol/l of butanol, SE3; 29.03 mmol/l of butanol, SE4; 28.16 mmol/l of butanol. The above Clostridia strain produced is known as *Clostridium thermobutanolicum* (SE Variant).

TABLE 2

Hypertonic Medium to Produce Protoplasts

| | |
|---|---|
| Ammonium Chloride | 1.0 g |
| Tris (Hydroxymethyl) aminomethan | 12.0 g |
| Potassium Chloride | 0.035 g |
| NaCl | 0.058 g |
| Na2SO4 | 0.3 g |
| KH2PO4 | 0.14 g |
| MgCl2 | 4.26 g |
| Glucose | 2.0 g |
| Sucrose | 68.46 g |
| L-leucine | 0.05 g |
| Distilled deionized water | 1.0 L |

TABLE 3

Protoplasting Medium

| | |
|---|---|
| Ammonium Chloride | 1.0 g |
| Tris (Hydroxymethyl) aminomethan | 12.0 g |
| Potassium Chloride | 0.035 g |
| NaCl | 0.058 g |
| Na2SO4 | 0.3 g |
| MgCl2 | 4.26 g |
| Sucrose | 68.46 g |
| Distilled deionized water | 1.0 L |

TABLE 4

Samples

| AT + TC (C. thermobutanolicum, SE variants) | Concentration, mM/L |
|---|---|
| SE1 | 28.66937 |
| SE2 | 29.03758 |
| SE3 | 28.00209 |
| SE4 | 27.48142 |
| SE5 | 27.28885 |
| SE6 | 27.35979 |
| SE7 | 25.20091 |
| SE8 | 28.16954 |
| SE9 | 38.90972 |

A deposit of the *Clostridium thermobutanolicum* disclosed above and cited in the appended claims has been made with the American Type Culture Collection (ATCC), University Boulevard, Manassas, Va. 20110-2209. The ATCC accession number for *Clostridium thermobutanolicum* is PTA-12350. The date of deposit for the *Clostridium thermobutanolicum* was Dec. 22, 2011. The deposit was made by Claflin University, 400 Magnolia Street, Orangeburg, S.C., 29115, since prior to the filing date of this application. Access to these deposits will be made available during the pendency of this application to persons determined by the Commissioner of Patent and Trademarks to be entitled thereto under 37 CFR 1.14 and 35 USC 122. Upon allowance of any claims in this application, all restriction on the availability to the public of the *Clostridium thermobutanolicum* will be irrevocably removed by affording access to the deposit with the ATCC. The deposit is intended to meet all of the requirements of 37 CFR §1.801-1.809. The deposit will be maintained in the depository for a period of thirty years, or five years after the last request, or for the effective life of the patent, whichever is longer, and will be replaced as necessary during that period.

While a preferred embodiment of the invention has been described using specific terms, such description is for illustrative purposes only, and it is to be understood that changes and variations may be made without departing from the spirit or scope of the following claims.

What is claimed is:

1. A thermophilic bacterial chimera comprising a fusion of *Clostridium acetobutylicum* (ATCC 824) and *Clostridium thermocellum* (ATCC 27405), wherein said thermophilic bacterial chimera has ATCC deposit number PTA-12350, wherein said chimera breaks down a biomass containing complex carbohydrates into glucose and converts glucose into biofuel, wherein said biofuel is selected from the group consisting of methanol, ethanol, propanol, butanol, and methane gas.

2. The thermophilic bacterial chimera of claim 1, wherein said chimera further breaks down a cellulosic biomass into glucose, converts glucose into butyric acid, $CO_2$ and $H_2$ and, converts butyric acid into butanol at thermophilic temperatures ranging from 45° C. to 65° C.

3. The thermophilic bacterial chimera of claim 1, wherein said biomass is selected from the group consisting of cellulosic biomass, lignocellulosic feedstock, and plant matter.

4. The thermophilic bacterial chimera of claim 1, wherein said biomass comprises wheat straw and/or pulping liquor.

5. A single-step, single-vessel method of converting a biomass into a biofuel, said method comprising the steps of:

a. combining a biomass comprising complex carbohydrates and the thermophilic bacterial chimera of claim 1;

b. permitting the thermophilic bacterial chimera to digest complex carbohydrates found in the biomass into glucose and other monosaccharides; and c. fermenting the glucose and other monosaccharides produced in step (b) into a biofuel, wherein said biofuel is selected from the group consisting of methanol, ethanol, propanol, butanol, and methane gas.

6. The method of claim 5, wherein said complex carbohydrates comprise cellulose.

7. The method of claim 5, wherein said biomass comprises cellulose.

8. The method of claim 5, wherein said biomass comprises a lignocellulosic feedstock.

9. The method of claim 5, wherein said biomass is derived from plant matter.

10. The method of claim 9, wherein said plant matter is wheat straw and/or pulping liquor.

11. The method of claim 5, wherein the fermentation step (b) takes place at a temperature at which butanol evaporates and under controlled vacuum conditions, such that the butanol may be continually evaporated and collected via a differential distillation and condensation process.

12. The method of claim 11, wherein the continual evaporation and collection processes prevents the level of butanol from reaching levels toxic to the thermophilic bacterial chimera.

13. The method of claim 5, wherein the digesting and fermenting of steps (b) and (c) take place at thermophilic temperatures ranging from 45° C. to 65° C.

* * * * *

UNITED STATES PATENT AND TRADEMARK OFFICE
CERTIFICATE OF CORRECTION

| | |
|---|---|
| PATENT NO. | : 8,669,082 B1 |
| APPLICATION NO. | : 13/592103 |
| DATED | : March 11, 2014 |
| INVENTOR(S) | : Omar Bagasra et al. |

Page 1 of 1

It is certified that error appears in the above-identified patent and that said Letters Patent is hereby corrected as shown below:

In the Specification

Column 1, line 5, insert the following text:

-- This invention was made with government support under N66001-10-1-4071 awarded by Defense Advanced Research Projects Agency. The government has certain rights in the invention. --

Signed and Sealed this
Twenty-fourth Day of February, 2015

Michelle K. Lee
*Deputy Director of the United States Patent and Trademark Office*